United States Patent [19]
Lassen

[11] Patent Number: 4,636,209
[45] Date of Patent: Jan. 13, 1987

[54] SANITARY NAPKIN WITH FLUID TRANSFER LAYER

[75] Inventor: Frederich O. Lassen, Winnebago County, Wis.

[73] Assignee: Kimberly-Clark Corporation, Neenah, Wis.

[21] Appl. No.: 754,804

[22] Filed: Jul. 12, 1985

Related U.S. Application Data

[63] Continuation of Ser. No. 472,708, Mar. 7, 1983, abandoned.

[51] Int. Cl.⁴ ............................................. A61F 13/16
[52] U.S. Cl. ..................................... 604/378; 604/370
[58] Field of Search ................ 604/378, 370, 366, 385

[56] References Cited

U.S. PATENT DOCUMENTS

| | | |
|---|---|---|
| 810,135 | 1/1906 | Green . |
| 3,143,113 | 8/1964 | Mills . |
| 3,291,131 | 12/1966 | Joa . |
| 4,397,644 | 8/1983 | Matthews et al. . |

Primary Examiner—C. Fred Rosenbaum
Assistant Examiner—Sherri E. Vinyard
Attorney, Agent, or Firm—J. J. Duggan; D. L. Traut; P. A. Leipold

[57] ABSTRACT

A sanitary napkin as provided with a multilayer absorbent, the top layer of which is designed to transfer fluid rapidly from the cover to secondary layers. The top layer contains at least 60% thermoplastic fiber and is oriented 90° from the axis of deposition of the web from which it was derived.

3 Claims, 1 Drawing Figure

SANITARY NAPKIN WITH FLUID TRANSFER LAYER

This is a continuation of copending application Ser. No. 472,708 filed on 3-7-83 now abandoned.

FIELD OF THE INVENTION

This invention relates to a sanitary napkin and particularly a sanitary napkin containing multiple layers of absorbent.

BACKGROUND OF THE INVENTION

Several features have been identified as desirable by users of sanitary napkins. Among these features are a dry surface adjacent the body and a napkin which is more comfortable than the traditional napkin after substantial amounts of fluid have been absorbed.

One of the difficulties inherent in a conventional sanitary napkin made of multiple layers of cellulosic material is that when fluid is absorbed by wood pulp fluff or similar cellulosic material the capillary walls tend to collapse inward. This collapse prevents fluid from being conducted downward through the capillaries and also substantially diminishes the inherent resiliency in the cellulosic material making the napkin relatively hard and uncomfortable when compared to its dry state.

A related problem is that after the capillaries collapse, fluid which would normally be conducted downward tends to remain at or near the top surface of the napkin and either rewets or fails to penetrate the cover providing a wet uncomfortable napkin surface.

Of course, the collapse of the capillaries in the uppermost portion of a cellulosic absorbent system prevents adequate utilization of the bottom portion of the absorbent because fluid fails to reach this area.

The problems of diminished comfort and downward direction fluid conductivity have been recognized and one of the proposed solutions has been to introduce thermoplastic fiber into an upper layer of a multilayer absorbent matrix. Examples of patents which teach the addition of thermoplastic material as an independent layer or as an admixture with conventional cellulose are U.S. Pat. Nos. 4,082,886 and 4,129,132 issued to George A. M. Butterworth et al; 3,976,074 issued to Harry G. Fitzgerald et al; 4,054,141 issued to Julius Schwaiger et al; 4,047,531 issued to Hamzeh Karama; 3,545,441 issued to Gunnar Gravdahl and 4,219,024 issued to Donald Patience et al.

While the presence of thermoplastic fibers either in combination with cellulosic fibers or by itself in the layer adjacent the cover adds resilience and minimizes a cell wall collapse, fluid conduction downward through this layer is minimized due to the enlarged capillary size present within the batt containing the thermoplastic fiber. While napkin constructions which utilize a thermoplastic fiber in an upper portion of an absorbent batt tend to feature conventional cellulosic absorbent materials below, the distance between the smaller capillaries present in the cellulosic portion and the cover substantially diminish the capillary attraction required to conduct the fluid downward. Relatively small amounts of fluid therefore are taken up by the principal absorbent component which is located towards the center of the napkin and the fluid tends to remain at or near the cover surface producing not only a napkin of substantially diminished capacity, but one with a wet, uncomfortable, top surface as well.

U.S. Pat. No. 3,143,113 by Victor Mills discloses a sanitary napkin containing multiple layers of cellulosic absorbent material with the uppermost layer formed from a web which has been turned 90° from its forming axis. This upper layer of absorbent is designed, according to the inventor, to help spread the fluid longitudinally.

SUMMARY OF THE INVENTION

According to this invention a sanitary napkin having multiple absorbent layers is provided in which the topmost layer positioned between a secondary principal absorbent layer and the cover contains substantial amounts of relatively rigid fibers defined heren as thermoplastic functional fibers. This top most layer is made from a web which has been turned 90° from its forming direction. These fibers perform as a hydrophobic "skeleton" to add rigidity to the wet web. While these fibers are conventionally of thermoplastic, it is possible to utilize normally hydrophillic fibers such as rayon or cotton which have been rendered hydrophobic either by cross linking, chemical treatment, etc. The term thermoplastic functional fibers is used generically to include both of these types of fibrous material.

This upper or topmost layer provides enhanced comfort due to the presence of thermoplastic fibers and a sufficient number of smaller capillaries to convey fluid from the cover into the second or principal absorbent layer with only slight levels of fluid retention within the topmost absorbent layer.

DETAILED DESCRIPTION OF THE INVENTION AND DRAWINGS

Figure 1:
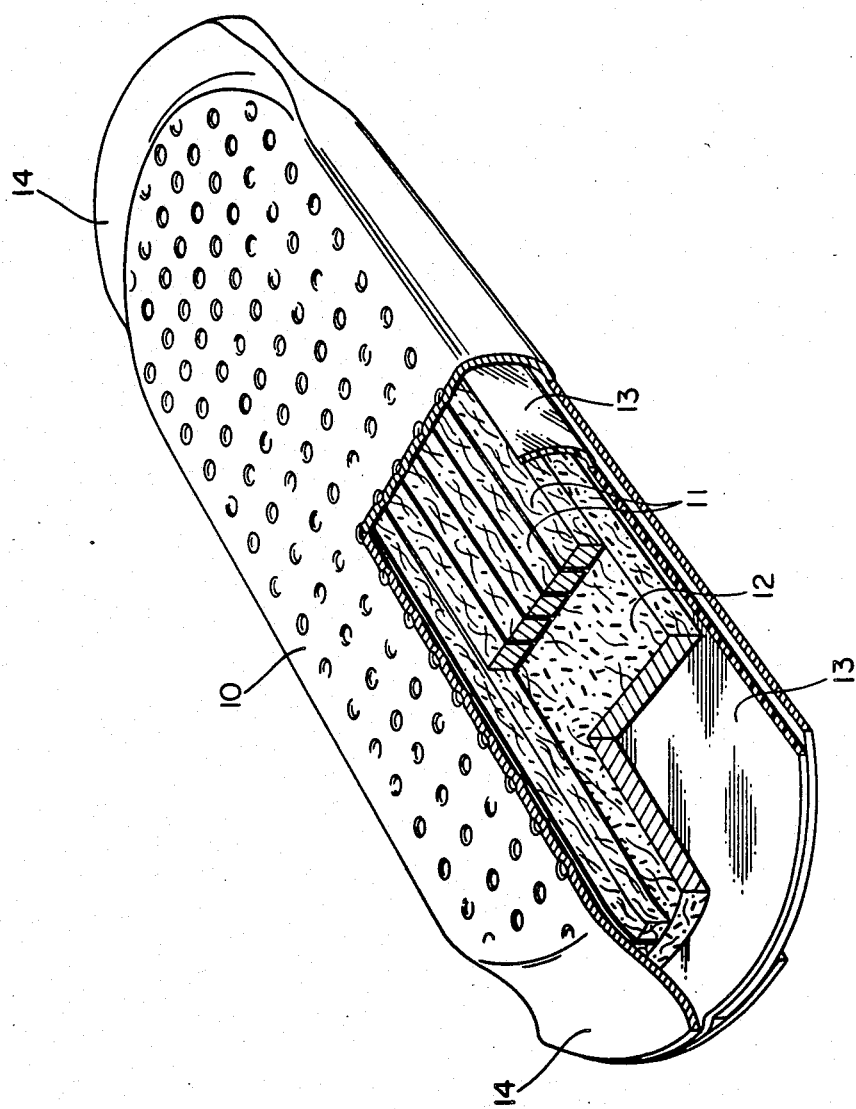

The invention may more readily be understood by reference to the drawings in which FIG. 1 is a perspective view partially in cross-section of an embodiment of this invention.

According to FIG. 1, a sanitary napkin is provided in which a fluid permeable cover 10 overwraps the other components. A top absorbent layer 11 is shown in the form of strips which extend longitudinally along the length of the napkin and overlie principal absorbent layer 12. A fluid impermeable baffle 13 is positioned under absorbent layer 12 and up the sides of the absorbent layer. The fluid impermeable baffle 12 is also covered by the fluid pervious cover 10. The napkin is sealed at either end leaving a free edge 14 which extends beyond the absorbent layer and the baffle. This seal can be done by adhesive or ultrasonic means and is not part of the invention.

The napkin is secured to the undergarment of the user by conventional means such as adhesive strips (not shown) located on the bottom of the napkin.

The web utilized to form absorbent layer 11 can be initially deposited by any of the conventional web forming techniques such as carding or deposition by a Rando Webber machine, etc. The method of forming the web will effect the initial orientation of fibers with webs formed by carding providing fibers primarily oriented in the machine direction while webs formed by the Rando Webber tend to provide a more random orientation of fibers. While either web can be used, it is preferred that the fibers in the top layer 11 are at least partially, randomly oriented rather than existing primarily in a single plane even if that plane is in the downward, i.e., z direction.

Once the web has been formed, a section of the web or a plurality of strips as shown in FIG. 1 are cut and turned 90° from the direction of fiber deposition.

It has been found that a density of between about 0.04 to 0.08 gms/cc. provides the most efficient level of fluid conduction from the cover to the principal absorbent layer and while this density level may vary to some extent depending upon the precise nature of the principal absorbent layer, i.e., if superabsorbent materials are included or other highly efficient absorbent systems provide a portion of that layer, these values have been found satisfactory when the absorbent layer is principally cellulosic in nature.

The top absorbent layer, as formed, should have at least 60% by weight and may have up to 80% by weight thermoplastic functional fiber to prevent capillary collapse within this layer. Fusible fibers are generally preferred because of the added web integrity which results from fiber fusing, although the presence of these fibers is not essential. It may be desirable to only fuse some of the fibers or none at all depending upon the other napkin components. It has also been found that at least 20% by weight of hydrophilic material should be present to aid in providing sufficient capillary attraction to pull the fluid through the cover and provide a resultant dry surface.

The thermoplastic functional fiber within this topmost layer should have a denier varying from 3 to 15.

It has been found in use tests that the topmost layer generally retains about 0.2 to 0.4 grams of exudate during the initial wetting period and that this level is not increased until the second or principal absorbent layer has been utilized to a level of 50–75%. Also, due to the orientation of the fibers there is minimum fluid flow along the longitudinal axis of the top layer and therefore the size of the stained area on the top of the pad is minimized. The size of the stain area as perceived by the consumer is directly related to napkin surface dryness.

What is claimed is:

1. A sanitary napkin comprising:
    a fluid permeable cover enclosing a multilayer fluid absorbent pad, said cover having a top side and a bottom side, said cover top side being placed adjacent a human body in use,
    said multilayer pad having a first layer of absorbent material adjacent said cover top side, and a second layer of absorbent material adjacent said first layer, said napkin having a longitudinal axis,
    said first layer formed from a planar web containing between about 60% and 80% by weight thermoplastic functional fibers to prevent capillary collapse of this layer, and at least about 20% by weight of hydrophilic absorbent material to draw fluid through said cover, wherein said planar web has a plane of deposition with fibers oriented in the X and Y direction of the plane of the web, and said first layer is comprised of a plurality of elongated portions cut from said web which are rotated 90° from said plane of deposition so at least some fibers are in the Z direction of said napkin and arranged side-by-side generally along said napkin longitudinal axis to yield said first layer,
    said first layer transferring fluid rapidly from said cover into said second layer with minimum fluid absorption until said second layer has exceeded about 50% of its absorbent capacity.

2. The napkin according to claim 1 wherein the denier of the fibers in the web of said first absorbent layer is between 3 and 15.

3. The napkin according to claim 1 wherein the web of said first absorbent layer has a density of 0.04 to 0.08 gms/cc.

* * * * *